United States Patent [19]

Dessel

[11] Patent Number: 5,429,623
[45] Date of Patent: Jul. 4, 1995

[54] GARMENT ATTACHABLE SLEEVE HOLDER FOR MEDICAL DRAIN RECEPTACLES

[75] Inventor: Arnold M. Dessel, Barrington, R.I.

[73] Assignee: Sil-Med Corporation, Taunton, Mass.

[21] Appl. No.: 87,063

[22] Filed: Jul. 7, 1993

[51] Int. Cl.⁶ ............................................. A61M 1/00
[52] U.S. Cl. ........................................ 604/317; 604/322
[58] Field of Search ............... 604/317, 319, 322–326; 224/148, 269; 24/3 L

[56] References Cited

U.S. PATENT DOCUMENTS

| 1,208,728 | 12/1916 | Bartlett et al. | 224/148 |
| 2,644,623 | 7/1953 | White | 224/148 |
| 4,341,212 | 7/1982 | Medwid | 604/317 |

Primary Examiner—Jerome L. Kruter
Attorney, Agent, or Firm—John M. Brandt

[57] ABSTRACT

This patent concerns a garment attachable sleeve holder for cushioning a vacuum operated tubular fluid receptacle wherein the sleeve provides a friction fit for the receptacle.

4 Claims, 1 Drawing Sheet

GARMENT ATTACHABLE SLEEVE HOLDER FOR MEDICAL DRAIN RECEPTACLES

BACKGROUND OF THE INVENTION

1. Field of the Invention

The invention resides in the field of holders and protectors for medical body drains and more particularly relates to a garment attachable sleeve for securing vacuum operated fluid recepticles.

2. Description of the Prior Art

An important part of post operative care includes the use of drain systems where by fluids which accumulate at a surgical location are removed by a needle inserted at the site, flexible tubing attached to the needle and an air evacuated glass tube connected to the flexible tubing. These devices are commercially sold under the tradename VACUTAINER. VACUTAINER is available from Becton Dickinson, Rutherford, N.J. 07070 and MONJECT is available from Sherwood Medical, St. Louis, Mo. 03103.

The draining process is slow and continuing over a period of time and requires the support of the tube by the patient so as to prevent disconnection of the tube or needle by stretching or breakage. Prevention of breakage is particularly important due to the contaminating effect of some body fluids in the current medical environment.

While the inventor knows of no relevant prior patent art in the field, a rigid molded plastic cover for the purpose of receiving the above described glass tube is commercially availble from Glassrock Products, Inc., Fairburn, Ga. 30213 under the tradename TLS—Surgical Drainage System.

SUMMARY OF THE INVENTION

The invention may be summarized as a garment attachable sleeve holder for medical drain recepticles in which an open ended sleeve composed of for example a flexible material such as silicon rubber is attached to a garment clip by a strap surrounding the sleeve. The sleeve is sized to provide a friction fit for the glass fluid receptacle or tube it is designed to receive.

The invention provides a direct and convenient way to secure drain tubes of the type described above. The flexible material of the sleeve cushions the tube to prevent breakage and as it is open ended allows easy insertion and withdrawal. The strap provides sufficient flexibility to allow some movement i.e. rotation of the holder to prevent rupture of the drain when the patient shifts position and the garment clip allows attachment at any suitable location.

These and other features and advantages of the invention will become more clear from the description of the preferred embodiment and drawings which follows.

DESCRIPTION OF THE PREFERRED EMBODIMENT

Figure 1:
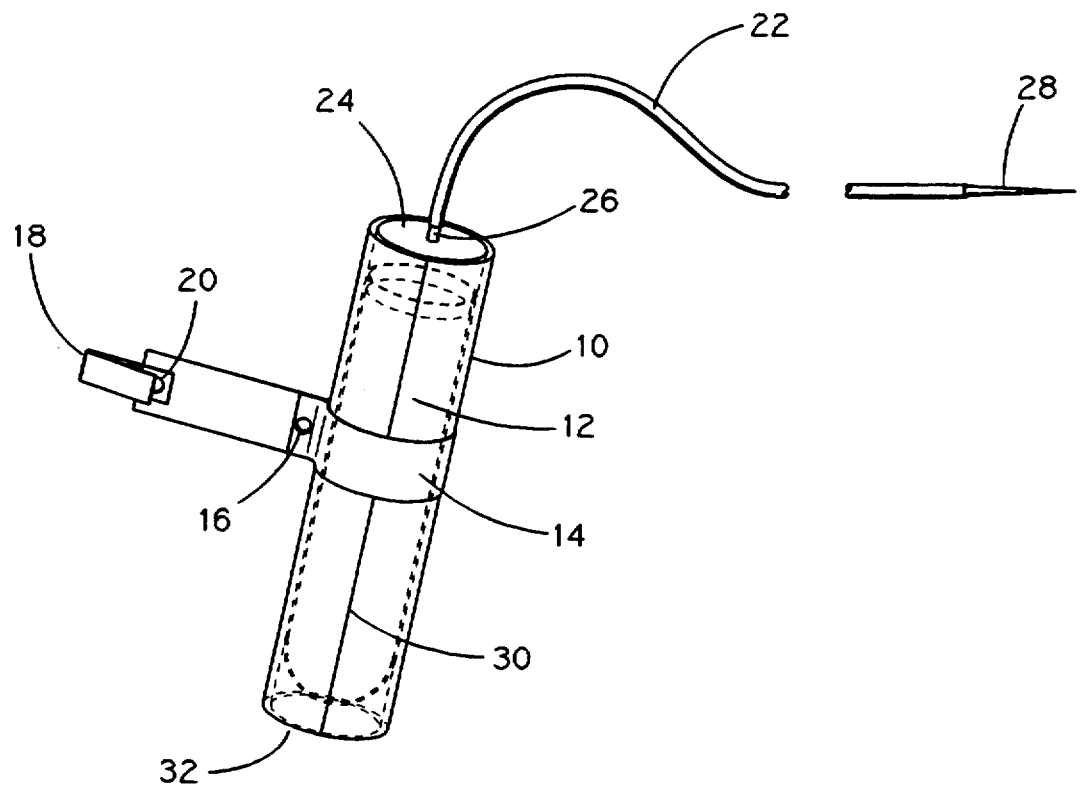
FIG. 1 is a perspective view of the preferred embodiment of the invention.

Referring to FIG. 1 there is shown a perspective view of the preferred embodiment of the invention in which sleeve holder 10 composed of for example translucent silicon rubber tubing is arranged to receive fluid drain receptacle 12. Strap 14 tightly surrounds holder 10 and may be attached by an adhesive, a heat seal, or rivet 16 as shown. Garment Clip 18 is attached to the end of strap 14 by rivet 20 and is used to attach the entire assembly at any suitable point on the garment.

Flexible tubing 22 extends from top 24 of receptacle 12 and is connected thereto by pipe 26. Hollow needle 28 is connected to the opposite end of tubing 22 and is inserted in the desired area to draw off fluids. As discussed above, receptacle 12 is under vacuum which causes fluid flow into the container.

Optionally, sleeve 10 may be separated by a longitudinal relief slit 30 to prevent binding of receptacle 12 in the holder. Receptacle 12 may be easily removed from the sleeve when filled, as observed through translucent material of the sleeve, by upward finger pressure through bottom port 32.

Figure 2:
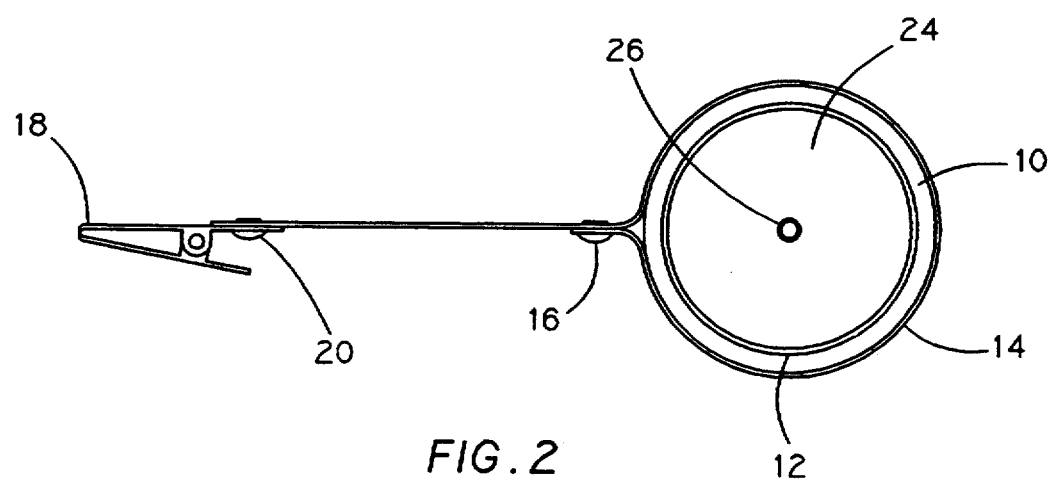
FIG. 2 is a top view of the embodiment of FIG. 1.

FIG. 2 is a top view of the holder of FIG. 1 wherein like numbers refer to like parts for purposes of clarification.

As variations obvious to those skilled in the art may be made in the above described embodiment, the scope of the invention is defined by the following claims.

What is claimed is:

1. A garment attachable sleeve holder for securing and cushioning a vacuum operated tubular fluid receptacle comprising in combination:
   a. an open ended flexible translucent tubular sleeve having an inside diameter about equal to the outside diameter of said receptacle and having a length greater than said receptacle, the inside diameter of said sleeve thereby providing a friction fit for said receptacle;
   b. a flexible strap surrounding and attached to said sleeve, said strap having a tail portion extending laterally from said sleeve; and
   c. a clip attached to said tail portion for gripping a garment.

2. The apparatus of claim 1 wherein said sleeve is comprised of silicon rubber.

3. The apparatus of claim 1 wherein said sleeve has a relief slit disposed along its length.

4. Apparatus for removing fluids from a surgical incision site comprising in combination:
   a. a hollow needle insertable into said site;
   b. a length of flexible tubing connected to and communicating with the bore of said needle;
   c. a sealed tubular receptacle under vacuum connected to and communicating with the bore of said tubing; and
   d. a garment attachable sleeve holder arranged to receive said receptacle comprising:
      1. an open ended flexible translucent tubular sleeve having an inside diameter about equal to the outside diameter of said receptacle and having a length greater than said receptacle, said inside diameter of said sleeve thereby providing a friction fit for said receptacle;
      2. a flexible strap surrounding and attached to said sleeve said strap having a tail portion extending laterally from said sleeve; and
      3. a clip attached to said tail portion for gripping a garment.

* * * * *